United States Patent
Berry et al.

(10) Patent No.: US 7,235,101 B2
(45) Date of Patent: Jun. 26, 2007

(54) REVISABLE PROSTHETIC DEVICE

(75) Inventors: Bret M. Berry, Cordova, TN (US); Eric C. Lange, Germantown, TN (US); Lukas Eisermann, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 331 days.

(21) Appl. No.: 10/662,928

(22) Filed: Sep. 15, 2003

(65) Prior Publication Data

US 2005/0060034 A1    Mar. 17, 2005

(51) Int. Cl.
*A61F 2/44* (2006.01)

(52) U.S. Cl. ............................. 623/17.11; 623/17.14
(58) Field of Classification Search ... 623/17.11–17.16
See application file for complete search history.

(56) References Cited

U.S. PATENT DOCUMENTS

| | | | |
|---|---|---|---|
| 5,258,031 A | 11/1993 | Salib et al. | |
| 5,401,269 A | 3/1995 | Buttner-Janz et al. | |
| 5,556,431 A | 9/1996 | Buttner-Janz | |
| 5,562,738 A | 10/1996 | Boyd et al. | |
| 5,658,335 A * | 8/1997 | Allen ................. | 623/17.16 |
| 5,674,284 A | 10/1997 | Chang et al. | |
| 5,674,296 A | 10/1997 | Bryan et al. | |
| 5,888,226 A | 3/1999 | Rogozinski | |
| 5,893,889 A | 4/1999 | Harrington | |
| 5,899,941 A | 5/1999 | Nishijima et al. | |
| 6,001,130 A | 12/1999 | Bryan et al. | |
| 6,063,121 A | 5/2000 | Xavier et al. | |
| 6,156,067 A | 12/2000 | Bryan et al. | |
| 6,176,882 B1 * | 1/2001 | Biedermann et al. .... | 623/17.15 |
| 6,375,682 B1 | 4/2002 | Fleischmann et al. | |
| 6,540,785 B1 | 4/2003 | Gill et al. | |
| 6,572,653 B1 * | 6/2003 | Simonson ................ | 623/17.13 |
| 2002/0077702 A1 | 6/2002 | Castro | |
| 2003/0135277 A1 | 7/2003 | Bryan et al. | |
| 2003/0187506 A1* | 10/2003 | Ross et al. ................ | 623/17.13 |
| 2004/0176843 A1 | 9/2004 | Zubok et al. | |
| 2004/0193271 A1* | 9/2004 | Fraser et al. ............. | 623/17.11 |
| 2005/0060034 A1 | 3/2005 | Berry et al. | |
| 2005/0228500 A1* | 10/2005 | Kim et al. ................ | 623/17.13 |

OTHER PUBLICATIONS

U.S. Appl. No. 10/423,712, Shipp, et al.

* cited by examiner

*Primary Examiner*—Bruce Snow
(74) *Attorney, Agent, or Firm*—Haynes and Boone, LLP

(57) ABSTRACT

A modular prosthetic device is described. The modular prosthetic device is provided with an anchoring device having first and second end members, the first and second end members cooperating to receive a prosthetic insertion device. The first and second end members each include a first surface, at least one vertebral-engaging member extending from the first surface, a second surface in an opposed relation to the first surface, and at least one flange extending from the second surface. The anchoring device is adapted to receive a variety of prosthetic insertion devices such that the modular prosthetic device can be revised into a variety of modular prosthetic devices. A stacking member is also provided for use with the anchoring device to provide a variety of modular, stackable prosthetic devices.

27 Claims, 12 Drawing Sheets

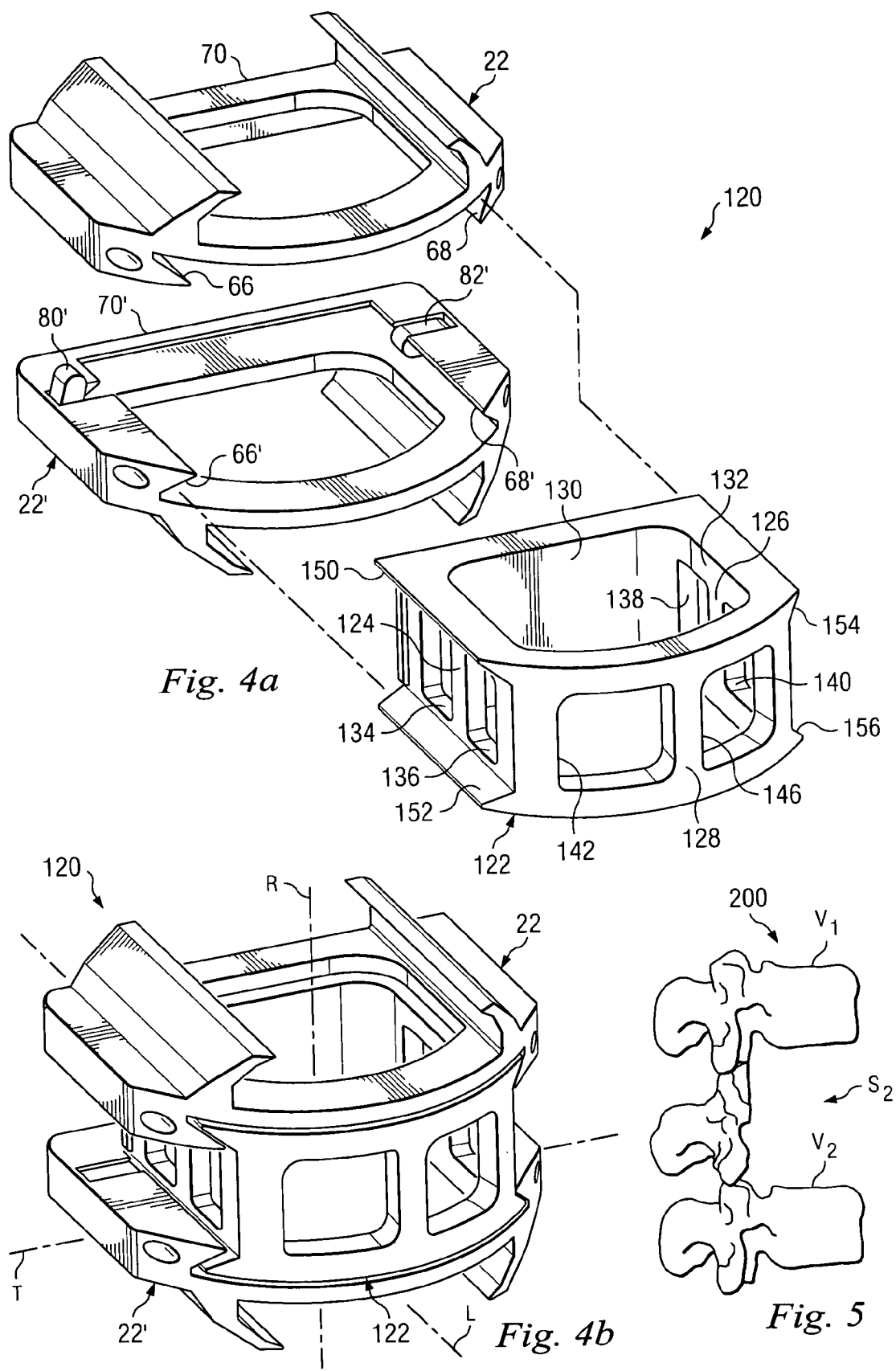

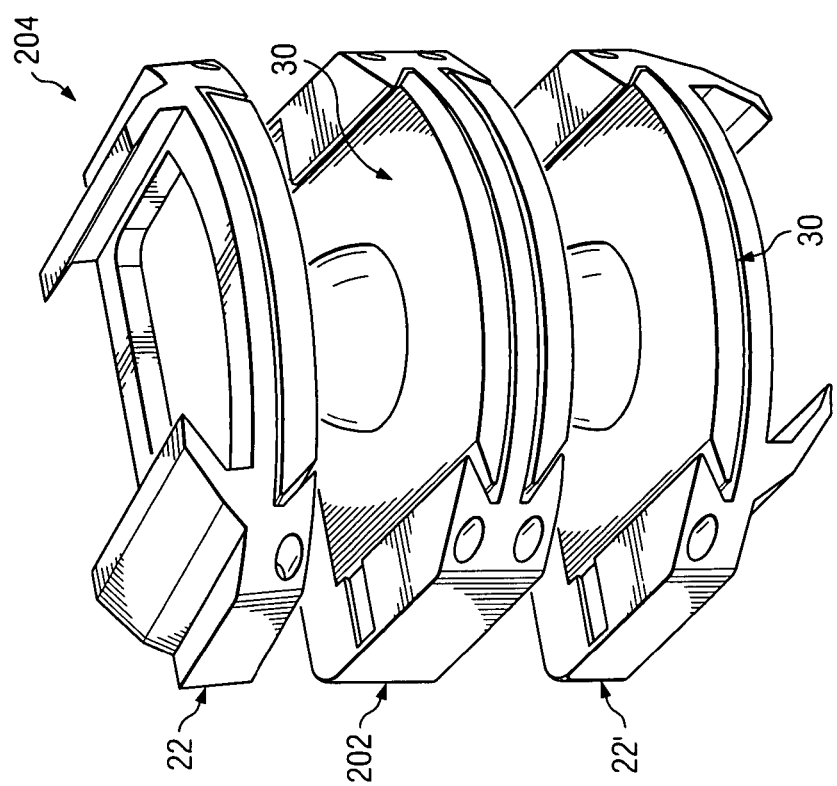
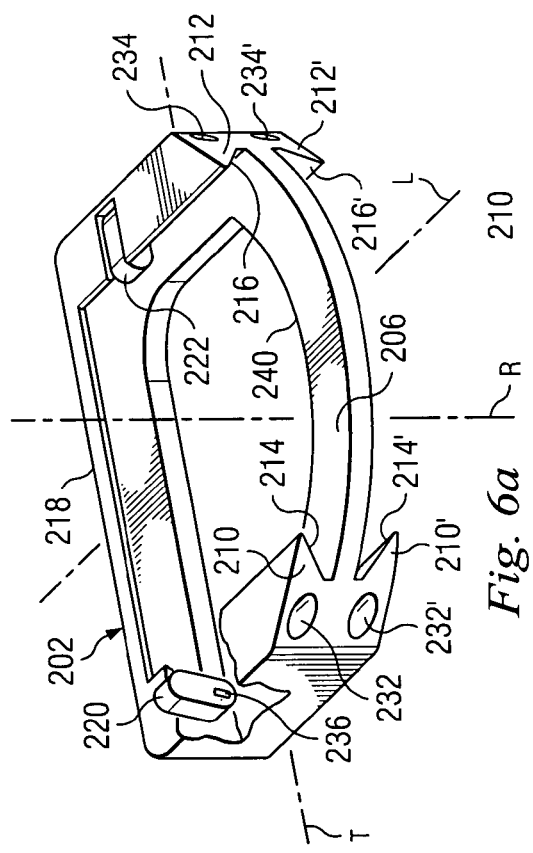
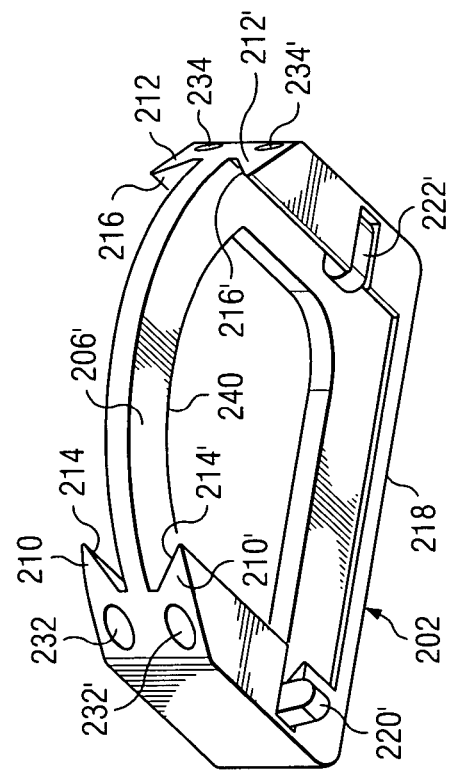

REVISABLE PROSTHETIC DEVICE

CROSS-REFERENCE TO RELATED APPLICATIONS

This application is related to U.S. Provisional Application No. 60/446,963 filed on Feb. 12, 2003, which is herein incorporated by reference for all legitimate purposes.

BACKGROUND

The present disclosure relates generally to the field of orthopedics and spinal surgery, and in some embodiments, the present disclosure relates to intervertebral prosthetic joints and fusion devices for use in the total or partial replacement of a natural intervertebral disc, and methods for implantation thereof.

In the treatment of diseases, injuries or malformations affecting spinal motion segments, and especially those affecting disc tissue, it has long been known to remove some or all of a degenerated, ruptured or otherwise failing disc. Other procedures, such as corpectomy and vertebrectomy, require the removal of an entire vertebral body in addition to the removal of an intervertebral disc. In cases involving intervertebral disc tissue and/or vertebral bodies that have been removed or are otherwise absent from a spinal motion segment, corrective measures are taken to ensure the proper spacing of the vertebrae formerly separated by the removed disc tissue and/or vertebral bodies.

Corrective measures can vary for different spinal procedures. For instance, in some cases, it is desirable to implement spinal devices that preserve motion between adjacent vertebral bodies. In other instances, spinal devices that promote fusion of adjacent vertebral bodies are the preferred corrective measure. Furthermore, continual monitoring of a patient having undergone a corrective spinal procedure may lead to a finding that the original corrective device needs to be replaced, or otherwise repaired.

Thus, what is needed is a spinal prosthetic device that is modular and revisable for use in a variety of corrective spinal procedures and methods of assembly thereof.

BRIEF DESCRIPTION OF THE DRAWINGS

FIG. 3a is an exploded view of a modular motion-preserving prosthetic device incorporating the end members of FIG. 2 according to one embodiment of the present disclosure.

FIG. 3b is an isometric view of the prosthetic device of FIG. 3a.

FIG. 4a is an exploded view of a modular prosthetic fusion device incorporating the end members of FIG. 2 according to another embodiment of the present disclosure.

FIG. 4b is an isometric view of the prosthetic device of FIG. 4a.

FIG. 5 is a lateral view of a pair of vertebral bodies depicting an intermediate vertebral body removed.

FIG. 6a is an isometric view of a stacking member for use in a modular prosthetic device according to one embodiment of the present disclosure.

FIG. 6b is an isometric view of the stacking member of FIG. 6a from a different angle.

FIG. 7b is an isometric view of the prosthetic device of FIG. 7a.

FIG. 8b is an isometric view of the prosthetic device of FIG. 8a.

FIG. 9b is an isometric view of the prosthetic device of FIG. 9a.

FIG. 10b is an isometric view of the prosthetic device of FIG. 10a.

FIG. 11b is an isometric view of the prosthetic device of FIG. 11a.

SUMMARY

Figure 1:
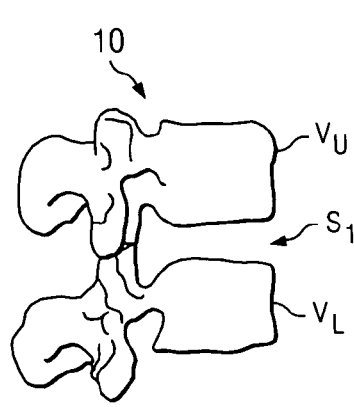
FIG. 1 is a lateral view of a pair of adjacent vertebral bodies.

An anchoring device for disposition within an intervertebral space is provided. The anchoring device includes first and second end members, the first and second end members cooperating to receive a prosthetic insertion device. The first and second end members each have a first surface, at least one vertebral-engaging member extending from the first surface, a second surface in an opposed relation to the first surface, and at least one flange extending from the second surface.

In another embodiment, an anchoring device for receiving a prosthetic insertion device is provided. The anchoring device includes a first end member having a first surface in an opposed relation to a second surface, a pair of vertebral-engaging members extending from the first surface, the vertebral-engaging members being angled towards one another, a pair of flanges extending from the second surface, the flanges being angled towards one another to define a pair of elongated slots, and a pair of cam devices positioned adjacent the elongated slots, the cam devices moveable between a first position and a second position. The anchoring device further includes a second end member cooperating with the first end member to receive a prosthetic insertion device, the second end member comprising a first surface in an opposed relation to a second surface, a pair of vertebral-engaging members extending from the first surface, the vertebral-engaging members being angled towards one another, a pair of flanges extending from the second surface, the flanges being angled towards one another to define a pair of elongated slots, and a pair of cam devices positioned adjacent the elongated slots, the cam devices moveable between a first position and a second position.

In yet another embodiment, an end member for receiving a portion of a prosthetic insertion device is provided. The end member includes a first surface, at least one vertebral-engaging member extending from the first surface, a second surface in an opposed relation to the first surface, and at least one flange extending from the second surface, and a locking mechanism for releasably securing a portion of a prosthetic insertion device.

In yet another embodiment, a modular prosthetic device is provided. The modular prosthetic device includes first and second end members each having at least one receiving portion and at least one locking mechanism positioned adjacent to the receiving portion. The modular prosthetic device further includes a prosthetic insertion device having an engaging portion for engaging the at least one receiving portion of the first and second end members, the prosthetic insertion device being adapted to be releasably secured to the first and second end members by the at least one locking mechanism of the first and second end members.

In yet another embodiment, a stacking member for use in forming a modular, stackable prosthetic device is provided. The stacking member includes a first surface in an opposed relation to a second surface, the first and second surfaces each having at least one flange to define a receiving portion, and a locking mechanism positioned adjacent to the receiving portion, the locking mechanism being movable between a first position and a second position.

In yet another embodiment, a modular, stackable prosthetic device is provided. The modular, stackable prosthetic device includes first and second end members each having at least one receiving portion, a stacking member positioned between the first and second end members, the stacking member having first and second surfaces, and at least one receiving portion defined along each of the first and second surfaces. The modular, stackable prosthetic device further includes a first prosthetic insertion device comprising an engaging portion for engaging the at least one receiving portion of the first end member, and an engaging portion for engaging the at least one receiving portion defined along the first surface of the stacking member, and a second prosthetic insertion device comprising an engaging portion for engaging the at least one receiving portion of the second end member, and an engaging portion for engaging the at least one receiving portion defined along the second surface of the stacking member.

In yet another embodiment, a modular prosthetic device is provided. The modular prosthetic device includes a first implant member having a first articular surface, a second implant member having a second articular surface, and a spacer member positioned between the first and second implant members, the spacer member having a third articular surface cooperating with the first articular surface to permit articulating motion between the spacer member and the first implant member, and a fourth articular surface cooperating with the second articular surface to permit articulating motion between the spacer member and the second implant member.

In yet another embodiment, a modular prosthetic device for insertion into a space created by a vertebrectomy is provided. The modular prosthetic device includes a first implant member adapted to engage a first vertebral body and having a first articular surface, a second elongated implant member adapted to engage a second vertebral body and having a second articular surface, the first and second articular surfaces cooperating to permit articulating motion between said first and second implant members. The second elongated implant member spans the space created by the vertebrectomy.

In yet another embodiment, a method for assembling a prosthetic device is provided. The method includes the steps of providing an anchoring device comprising first and second end members, the first and second end members having slots defined therein, providing a prosthetic insertion device having end portions corresponding to the slots defined in the anchoring device, aligning the end portions of the prosthetic insertion device with the slots of the anchoring device, and inserting the prosthetic insertion device into the anchoring device via the cooperation of the end portions and the slots.

DESCRIPTION

The present disclosure relates to modular spinal implants, and more particularly, to modular spinal implants that can be revised according to particular spinal procedures. For the purposes of promoting an understanding of the principles of such disclosure, reference will now be made to the embodiments, or examples, illustrated in the drawings and specific language will be used to describe the same. It will nevertheless be understood that no limitation of the scope of the disclosure is thereby intended. Any alterations and further modifications in the described embodiments, and any further applications of the principles of the disclosure as described herein are contemplated as would normally occur to one skilled in the art to which the disclosure relates. As such, individual features of separately described embodiments can be combined to form additional embodiments.

Referring to FIG. 1, shown therein is a lateral view of a portion of a spinal column 10, illustrating adjacent upper and lower vertebral bodies $V_U$, $V_L$ separated by a space S1 created by the removal of an intervertebral disc. The natural disc that would have been positioned between the two vertebral bodies $V_U$, $V_L$ is typically removed via a discectomy or a similar surgical procedure, the details of which would be known to one of ordinary skill in the art. It is desired to insert a prosthetic device into the space S1 to restore the structural integrity of the spinal column 10 upon removal of the intervertebral disc.

Figure 2A:
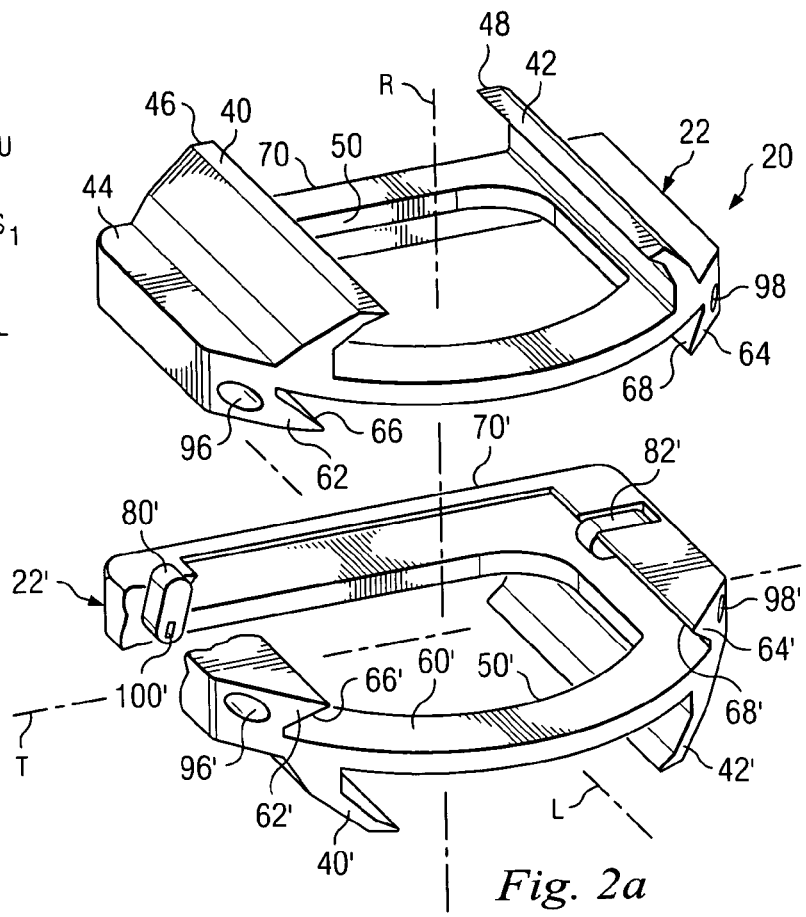
FIG. 2a is an isometric view of a pair of end members for use in a modular prosthetic device according to one embodiment of the present disclosure.
Figure 2B:
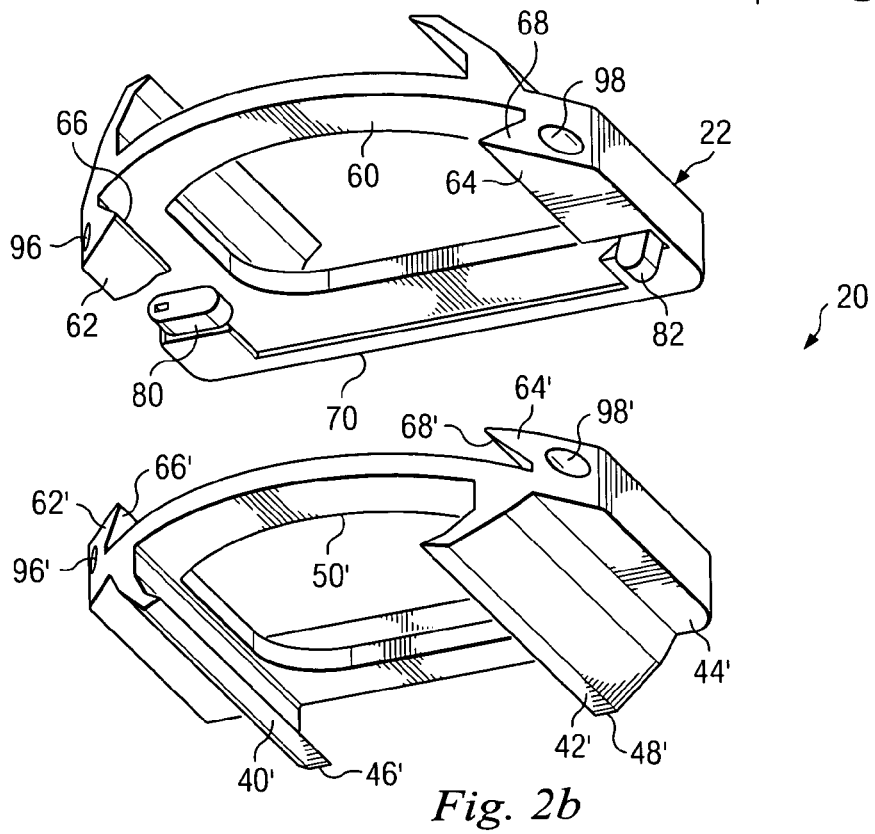
FIG. 2b is an isometric view of the pair of end members of FIG. 2a from a different angle.

Referring to FIGS. 2a and 2b, an anchoring device is generally referred to by the reference numeral 20. In one embodiment, the anchoring device 20 extends generally along a longitudinal axis L and includes a pair of substantially identical, yet inverted, end members 22, 22'. For purposes of this specification, substantially identical components will be given the same reference numerals. Although substantially identical components are given the same reference numerals, the lower end member 22' as viewed in FIGS. 2a and 2b and its components are given an apostrophe ("'") to simplify the following explanation of the anchoring device 20.

Although the end members 22, 22' of the anchoring device 20 may be formed from a wide variety of materials, in one embodiment of the disclosure, the end members 22, 22' are formed of a cobalt-chrome-molybdenum metallic alloy (ASTM F-799 or F-75). However, in alternative embodiments of the disclosure, the end members 22, 22' may be formed of other materials such as titanium or stainless steel, a polymeric material such as polyethylene, or any other biocompatible material that would be apparent to one of ordinary skill in the art.

The end members 22, 22' of the anchoring device 20 are adapted to receive a variety of prosthetic insertion devices for forming a variety of modular prosthetic devices. For example, and referring now to FIGS. 3a and 3b, the anchoring device 20 may be used in conjunction with a motion-preserving device 30 to form a modular prosthetic joint 32, which may then be inserted into the space S1 (FIG. 1) to engage the upper and lower vertebral bodies $V_U$, $V_L$.

In one embodiment, the motion-preserving device 30 is configured as a ball and socket device and thus includes a socket component 34 and a ball component 36. Although not depicted, other motion-preserving devices are contemplated for use with the anchoring device 20 such as devices formed of polymer or hydro gel that can replicate the movement of a healthy disc. The socket and ball components 34 and 36 may be formed of a variety of materials including, but not limited to, PEEK, stainless steel, UHMWPE, cobalt chrome, zirc coated materials and ceramics. The modular prosthetic joint 32 provides relative pivotal and rotational movement between the adjacent vertebral bodies to maintain or restore motion substantially similar to the normal bio-mechanical motion provided by a natural intervertebral disc. More specifically, the motion-preserving device 30 permits the end members 22, 22' to pivot relative to one another about a number of axes, including lateral or side-to-side pivotal movement about longitudinal axis L and anterior-posterior pivotal movement about a transverse axis T.

Furthermore, the motion-preserving device 30 permits the end members 22, 22' to rotate relative to one another about a rotational axis R. Although the modular prosthetic joint 32 has been illustrated and described as providing a specific combination of articulating motion, it should be understood that other combinations of articulating movement are also possible, such as, for example, relative translational or linear motion, and such movement is contemplated as falling within the scope of the present disclosure.

For sake of brevity, only the end member 22 will now be described in detail. Referring to FIGS. 2a–3b, the end member 22 includes a pair of fins 40, 42 longitudinally extending along a substantial portion of an outer surface 44. Although only two fins 40, 42 are shown, it is understood that one or several fins are contemplated to extend from the outer surface 44. The fins 40, 42 are provided for engaging an adjacent vertebral body, such as $V_U$ in FIG. 1. To facilitate such engagement, in one embodiment, the fins 40, 42 are angled towards one another and each include a sharp edge 46, 48, respectively. It is understood, however, that the fins 40, 42 may be configured in any shape that facilitates the functional demands of the fins such as a tapered or orthogonal (relative to the outer surface 44) configuration and that the edges 46, 48 may be formed on opposite portions of the fins as viewed in FIGS. 2a–3b.

In one embodiment, it may be beneficial to fuse the end member 22 to the vertebral body $V_U$. To facilitate such fusing, the fins 40, 42 and the outer surface 44 may be coated with a bone-growth promoting substance, such as, for example, a hydroxyapatite coating formed of calcium phosphate. Additionally, the fins 40, 42 and the outer surface 44 may be roughened prior to being coated with the bone-growth promoting substance to further enhance bone on-growth. Such surface roughening may be accomplished by way of, for example, acid etching, knurling, application of a bead coating, or other methods of roughening that would occur to one of ordinary skill in the art. Still further, a hole 50 may be formed through the end member 22 in a direction along the rotational axis R to further promote bone-growth between the end member 22 and the adjacent vertebral body $V_U$.

The end member 22 further includes an inner surface 60 (FIG. 2b), which, in one embodiment, is in an opposed relation to the outer surface 44. In one embodiment, a pair of angled flanges 62, 64 depend towards one another from the inner surface 60 and extend longitudinally along a substantial portion of the inner surface to define a pair of elongated slots 66, 68, respectively. Although depicted as dovetail in shape, the slots 66, 68 may have any number of configurations such as keyway, L, or curved configurations, and thus the flanges 62, 64 may take any number of shapes to define the slots.

The slots 66, 68 are open at an anterior portion of the end member 22 (depicted as the front portion of the end member as viewed in FIGS. 2a and 2b) in order to receive corresponding portions of the socket component 34 of the motion preserving device 30. The slots 66, 68 are sealed off at a posterior portion of the end member 22 (depicted as the back portion of the end member as viewed in FIGS. 2a and 2b) via a posterior wall 70 of the end member. The posterior wall 70 provides a stop against which the socket component 34 abuts upon full insertion into the end member 22 as will be described. It is understood that reference to anatomical directions in this specification such as anterior, posterior and lateral is for purposes of clarification only, and is not intended to limit the modular prosthetic joint 32 (or the additional embodiments described herein) to a specific orientation relative to such anatomical directions. As such, the posterior portion of the end member 22 may be open and the anterior portion closed, or the open and closed portions may be defined in lateral directions.

To facilitate engagement with the end member 22, the socket component 34 includes a pair of tapered end portions 72, 74, which are adapted to fit into the slots 66, 68. As with the slots 66, 68, the end portions 72, 74 of the socket component 34 may have any number of configurations so long as the end portions can engage the slots 66, 68.

In one embodiment, the end member 22 further includes a pair of cam devices 80, 82 (FIG. 2b), which are positioned adjacent to the slots 66, 68, respectively, and aid in securing the socket component 34 to the end member. In one embodiment, the cam devices 80, 82 each engage a cam slot (one of which is depicted as 88) formed in the socket component 34 to retain the socket component 34 to the end member 22 upon insertion therein. The cam devices 80, 82 are movable between an open position (cam device 82 in FIG. 2b) and a closed position (cam device 80 in FIG. 2b) via a tool (not depicted), which is insertable through a pair of access holes 96, 98, respectively. In one embodiment, an elongated slot 100 (FIG. 2b) is formed in the cam device 80 such that a tool may engage the slot to actuate the cam device between the open and closed positions. Although not shown, it is understood that cam device 82 includes an elongated slot substantially identical to slot 100. Furthermore, the cam devices 80, 82 may be in a frictional engagement with the end member 22, which allows the cam devices to be maintained in the open and closed positions without regard to gravity. It is understood that other locking mechanisms other than the depicted cam devices 80, 82 are contemplated for use with the anchoring device 20 such as pressure fits or slot and peg assemblies. It is also understood that no locking mechanism may be necessary and the end member 22 receives a prosthetic insertion device in a frictional engagement.

As discussed previously, the end member 22' is substantially similar to the end member 22 and thus includes a pair of fins 40', 42' having a pair of sharp edges 46', 48', an outer surface 44', a hole 50', an inner surface 60', a pair of angled flanges 62', 64' defining a pair of elongated slots 66', 68', a posterior wall 70', a pair of cam devices 80', 82', a pair of access holes 96', 98', and an elongated slot (one of which is shown as 100' in FIG. 2a) formed in each cam device. The end member 22' is adapted to receive and retain the ball component 36 of the motion-preserving device 30 in substantially the same manner as the end member 22 receives and retains the socket component 34 described above. As such, to facilitate engagement with the end member 22', the ball component 36 includes a pair of tapered end portions 102, 104, which are adapted to fit into the slots 66', 68'. It is understood that the socket and ball components 34, 36 are interchangeable between the end members 22, 22'.

Figures 3A, 3B:
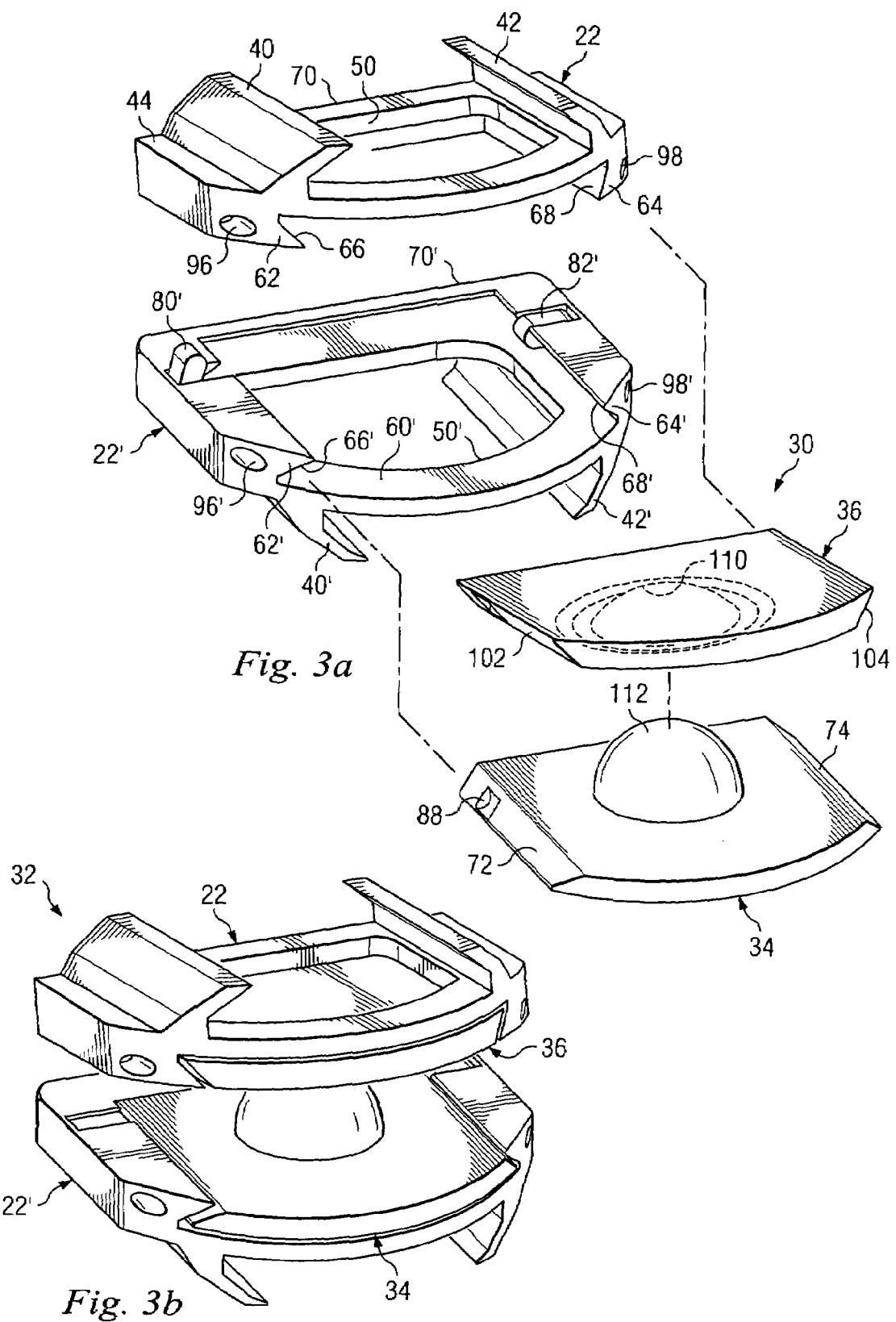

Referring now to FIGS. 3a and 3b, and turning now to a more detailed discussion of the motion-preserving device 30, in one embodiment, the socket component 34 includes a recess 110. In one embodiment, the recess 110 has a concave shape, and is configured as a spherical-shaped socket. However, it should be understood that other configurations of the recess 110 are also contemplated, such as, for example, cylindrical, elliptical or other arcuate configurations or possibly non-arcuate configurations. Moreover, although the recess 110 is depicted as being formed in a raised portion of the socket component 34, it is understood that the socket component may be of sufficient thickness to have a recess formed therein without need for the raised portion. The remaining portion of the socket component 34 can be tapered or otherwise configured to facilitate the insertion of the socket component into the end member 22.

In one embodiment, the ball component 36 includes a projection 112 having a convex shape, which may be configured as a spherical-shaped ball (half of which is shown). It should be understood that other configurations of the projection 112 are also contemplated, such as, for example, cylindrical, elliptical or other arcuate configurations or possibly non-arcuate configurations. It should also be understood that the remaining portion of the ball component 36 may take on planar or non-planar configurations, such as, for example, a tapered configuration extending from the projection 112 to the end portions 102, 104.

Although the convex projection 112 is illustrated as having a generally smooth, uninterrupted surface, it should be understood that a surface depression or cavity may be defined along a portion of the projection to provide a means for clearing out matter, such as particulate debris, that is disposed between the abutting socket and ball components 34, 36. In such case, the convex surface of the recess 110 may alternatively define a generally smooth, uninterrupted surface. In another embodiment, each of the convex projection 112 and the concave recess 110 may define a surface depression to facilitate removal of particulate matter disposed between the abutting ball and socket components 34, 36. In still another embodiment, the convex projection 112 may have a generally smooth, uninterrupted surface and the concave recess 110 may include a surface depression or cavity defined along the surface thereof.

In operation, the modular prosthetic joint 32 may be assembled by preparing the end member 22 to receive the socket component 34 by actuating the cam devices 80, 82 to an open position. The end portions 72, 74 of the socket component 34 are then aligned with the slots 66, 68 of the end member 22 and the socket component is inserted into the end member to the point of making contact with the posterior wall 70. The cam devices 80, 82 are then actuated via a tool (not shown) to a closed position, thereby securing the socket component 34 to the end member 22.

In a like manner, the end member 22' is prepared for receiving the ball component 36 by actuating the cam devices 80', 82' to an open position. The end portions 102, 104 of the ball component 36 are then aligned with the slots 66', 68' of the end member 22' and the ball component is inserted into the end member to the point of making contact with the posterior wall 70'. The cam devices 80', 82' are then actuated via a tool (not shown) to a closed position, thereby securing the ball component 36 to the end member 22'.

The above-described assemblage processes may take place prior to or after insertion of the end members 22, 22' into the vertebral bodies $V_U$, $V_L$ (FIG. 1). Furthermore, cuts can be formed in the vertebral bodies $V_U$, $V_L$ to receive the fins 40, 42 and 40', 42' of the end members 22, 22', respectively, or the fins themselves, via the edges 46, 48 and 46', 48', can be used to cut into the vertebral bodies. It is understood that the modular prosthetic joint 32 (and the additional embodiments described herein) may be inserted into the disc space S1 between the vertebral bodies $V_U$, $V_L$ from a variety of approaches including, but not limited to, the anterior, oblique and lateral approaches.

As can be appreciated, a variety of prosthetic insertion devices other than the motion-preserving device 30 can be used with the anchoring device 20. For example, in some instances it may be desirable to replace the motion-preserving device 30 with a fusion member. In such circumstances, it may be preferable to replace only the motion-preserving device 30 and not the anchoring device 20. As such, the modular prosthetic joint 32 can be revised into a modular prosthetic fusion device without having to discard, or otherwise replace, the anchoring device 20.

Referring now to FIGS. 4a and 4b, a modular prosthetic fusion device 120 may be inserted into the space S1 between the vertebral bodies $V_U$, $V_L$ (FIG. 1) to promote fusion therebetween. In one embodiment, the modular prosthetic fusion device 120 includes a fusion cage 122, which is insertable into the end members 22, 22'. It is understood that a variety of other fusion members are contemplated for use with the end members 22, 22' other than the fusion cage 122. The fusion cage 122 may be formed of a variety of materials including, but not limited to, PEEK, stainless steel, UHM-WPE, cobalt chrome, zirc coated materials and ceramics.

In one embodiment, the fusion cage 122 is a unitary structure that includes a pair of lateral walls 124, 126, an anterior wall 128 and a posterior wall 130, all of which define an opening 132 through the fusion cage 122 along a rotational axis R. The opening 132 promotes fusing bone growth between the vertebral bodies $V_U$, $V_L$ (FIG. 1). A plurality of apertures 134, 136, 138, 140, 142, 146 maybe formed through the lateral 124, 126 and anterior 128 walls to further encourage bone growth. Like the end members 22, 22', the fusion cage 122 may be coated with a bone-growth promoting substance, such as, for example, a hydroxyapatite coating formed of calcium phosphate. Additionally, the fusion cage 122 may be roughened prior to being coated with the bone-growth promoting substance to further enhance bone on-growth. Such surface roughening may be accomplished by way of, for example, acid etching, knurling, application of a bead coating, or other methods of roughening that would occur to one of ordinary skill in the art.

To accommodate insertion of the fusion cage 122 into the end members 22 and 22', a tapered extension 150, 152, 154, 156 extends longitudinally along a substantial portion of each edge of each lateral wall 124, 126. The tapered extensions 150, 154 are adapted to fit into the slots 66, 68 of the end member 22 and the tapered extensions 152, 156 are adapted to fit into the slots 66', 68' of end member 22'. The tapered extensions 150, 152, 154, 156 and the slots 66, 66', 68, 68' may have any number of configurations so long as the slots can receive the fusion cage 122 in a corresponding engagement.

In operation, the modular prosthetic fusion device 120 may be assembled by preparing the end members 22 and 22' to receive the fusion cage 122 by actuating the cam devices 80, 80', 82, 82' to an open position. The tapered extensions 150, 152, 154, 156 of the fusion cage 122 are then aligned with the slots 66, 66', 68, 68' of the end members 22, 22' and the fusion cage 122 is inserted into the end members to the point of making contact with the posterior walls 70, 70'. The cam devices 80, 80', 82, 82' are then actuated via a tool (not shown) to a closed position, thereby securing the fusion cage 122 to the end members 22, 22'.

By way of example, and to illustrate the revisable aspect of the anchoring device 20, the motion-preserving device 30 may be disposed within the anchoring device prior to insertion of the fusion cage 122. Thus, prior to inserting the fusion cage 122 in the process described above, the motion-preserving device 30 can be removed from the anchoring device 20 by simply opening the cam devices 80, 80', 82, 82' and extracting the socket and ball components 34, 36 in an anterior direction.

The anchoring device 20 is contemplated for use not only with modular prosthetic devices for insertion between adjacent vertebral bodies $V_U$, $V_L$ (FIG. 1) after discectomy, but also for use in stabilizing regions of the spine in the aftermath of more complex procedures such as corpectomy and vertebrectomy procedures.

Referring to FIG. 5, shown therein is a lateral view of a portion of a spinal column 200, illustrating a pair of vertebral bodies $V_1$, $V_2$ separated by a space S2 created by the removal of a pair of intervertebral discs and an intervertebral body that had been positioned between the vertebral bodies $V_1$, $V_2$. In one embodiment, the natural disc and vertebral body that would have been positioned between the two vertebral bodies $V_1$, $V_2$ is typically removed via a corpectomy or vertebrectomy or a similar surgical procedure, the details of which would be known to one of ordinary skill in the art. It is desired to insert a prosthetic device into the space S2 to restore the structural integrity of the spinal column 200 upon removal of the intervertebral discs and vertebral body.

Referring to FIGS. 6a and 6b, a stacking member 202 may be used in conjunction with the anchoring device 20 to form a modular stackable prosthetic joint 204 (FIGS. 7a and 7b), which can be inserted into the space S2 (FIG. 5). In one embodiment, the upper portion of the stacking member 202 (as viewed in FIGS. 6a and 6b) is substantially identical to the lower portion of the stacking member except for the inverted relationship between the upper and lower portions, and as such, the components of the lower portion of the stacking member are given an apostrophe ("'") to simplify the following explanation of the stacking member. In one embodiment, the stacking member 202 includes an upper surface 206 (as viewed in FIGS. 6a and 6b) in an opposed relation to a lower surface 206'. A pair of angled flanges 210, 212 depend towards one another from the upper surface 206 and extend longitudinally along a substantial portion of the upper surface 206 to define a pair of elongated slots 214, 216, respectively. Although depicted as dovetail in shape, the slots 214, 216 may have any number of configurations such as keyway, L, or curved configurations, and thus the flanges 210, 212 may take any number of shapes to define the slots.

The slots 214, 216 are open at an anterior portion of the end member (as viewed in FIGS. 6a and 6b) in order to receive corresponding portions of a variety of prosthetic insertion devices as will be described. The slots 214, 216 are sealed off at a posterior portion of the end member 22 (as viewed in FIGS. 6a and 6b) via a posterior wall 218 of the stacking member 202. The posterior wall 218 provides a stop against which a prosthetic insertion device abuts upon full insertion into the upper portion of the stacking member (as viewed in FIGS. 6a and 6b).

The stacking member 202 further includes a pair of cam devices 220, 222, which are positioned adjacent to the slots 214, 216, respectively, and aid in securing a prosthetic device to the stacking member. The cam devices 220, 222 each engage a cam slot (not shown) formed in a prosthetic insertion device to be inserted into the upper portion of the stacking member 202.

The cam devices 220, 222 are movable between an open position (220 in FIG. 6a) and a closed position (222 in FIG. 6a) via a tool (not depicted), which is insertable through a pair of access holes 232, 234, respectively. In one embodiment, an elongated slot 236 is formed in the cam device 220 such that a tool may engage the slot to actuate the cam device between the open and closed positions. Although not shown, it is understood that the cam device 222 includes an elongated slot substantially identical to slot 236. Furthermore, the cam devices 220, 222 may be in a frictional engagement with the stacking member 202, which allows the cam devices to be maintained in the open and closed positions without regard to gravity. It is understood that other locking mechanisms other than the depicted cam devices 220, 222 are contemplated for use with the stacking member 202 such as pressure fits or slot and peg assemblies. It is also understood that no locking mechanism may be necessary and the stacking member 202 receives a prosthetic insertion device in a frictional engagement.

The lower portion of the stacking member 202 is substantially similar to the upper portion of the stacking member (as viewed in FIGS. 6a and 6b) and thus includes a lower surface 206' (corresponding to upper surface 206), a pair of angled flanges 210', 212' defining a pair of elongated slots 214', 216', a pair of cam devices 220', 222', a pair of access holes 232', 234', and an elongated slot (not shown) formed in each cam device. The upper and lower portions of the stacking member 202 share the same posterior wall 218. Furthermore, a hole 240 may be formed through the stacking member 202 to define an opening through which bone growth may occur as will be described.

Figure 7A:
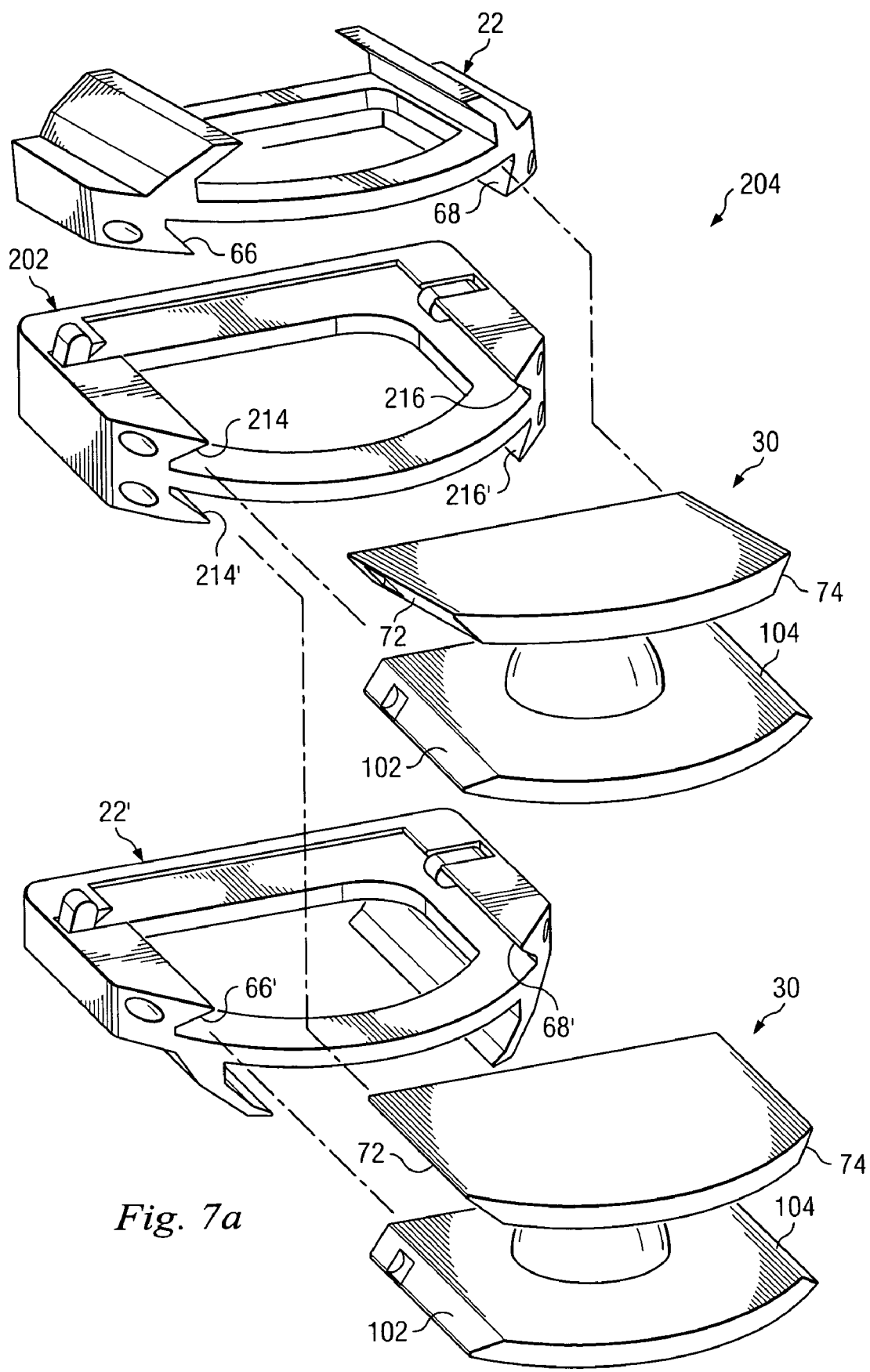
FIG. 7a is an exploded view of a modular motion-preserving prosthetic device incorporating the end members of FIGS. 2a and 2b and the stacking member of FIGS. 6a and 6b according to one embodiment of the present disclosure.

Referring now to FIGS. 7a and 7b, a pair of motion-preserving devices substantially identical to the motion-preserving device 30 may be used in conjunction with the anchoring device 20 and the stacking member 202 to form the modular stackable prosthetic joint 204. In operation, the modular stackable prosthetic joint 204 may be assembled by aligning the end portions 72, 74 of the upper motion-preserving device 30 (as viewed in FIGS. 7a and 7b) with the slots 66, 68 of the upper end member 22 and aligning the end portions 102, 104 with the slots 214, 216 of the stacking member 202. The upper motion-preserving device 30 may then be inserted into the upper end member 22 and the stacking member 202.

In a like manner, the lower motion-preserving device 30 (as viewed in FIGS. 7a and 7b) may be assembled into the modular stackable prosthetic joint 204 by aligning the end portions 72, 74 of the lower motion-preserving device with the slots 214', 216' of the stacking member 202 and aligning the end portions 102, 104 with the slots 66', 68' of the lower end member 22' (as viewed in FIGS. 7a and 7b). The lower motion-preserving device 30 may then be inserted into the stacking member 202 and the lower end member 22' to complete the assembly of the modular stackable prosthetic joint 204.

Figure 8A:
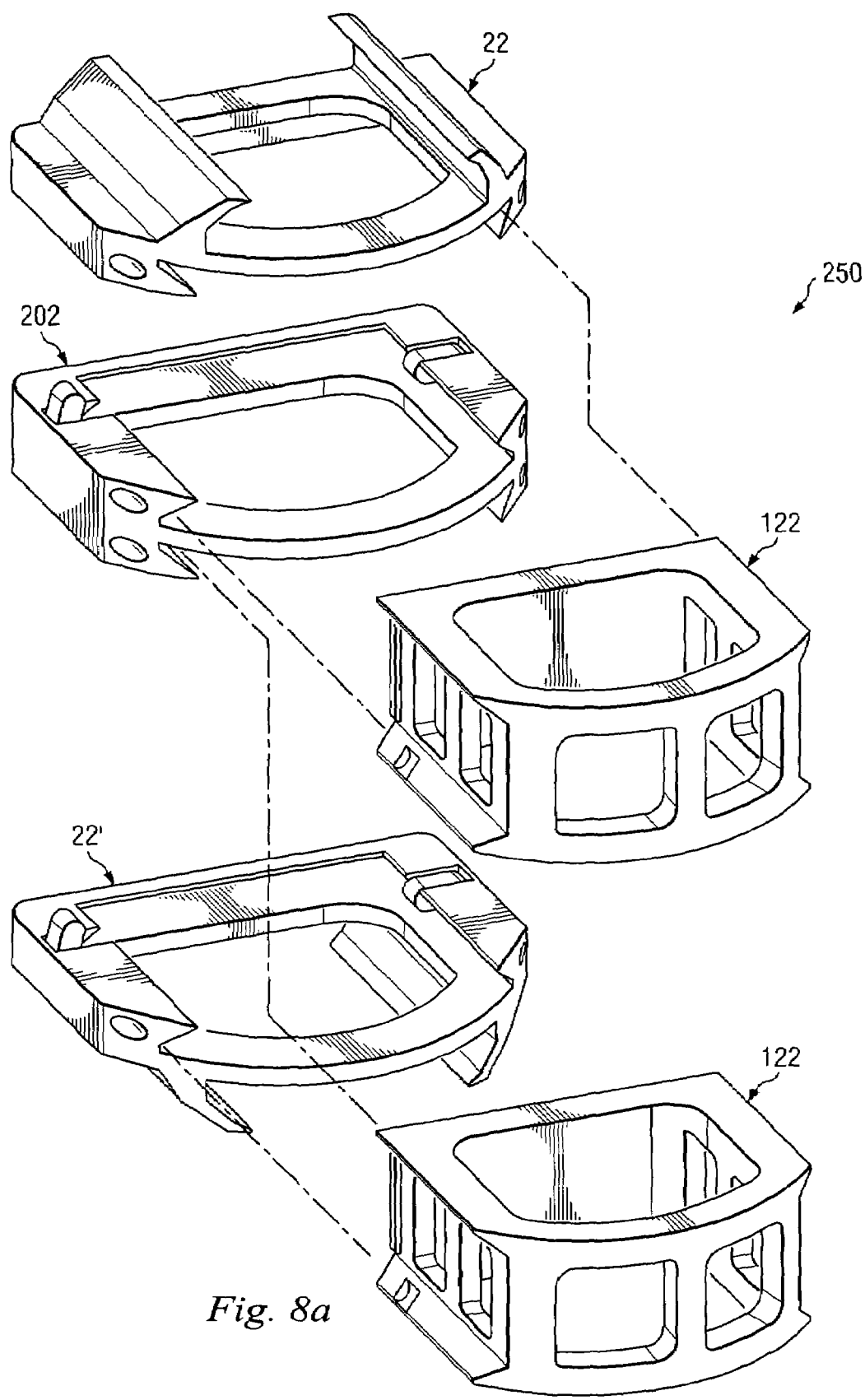
FIG. 8a is an exploded view of a modular prosthetic fusion device incorporating the end members of FIGS. 2a and 2b and the stacking member of FIGS. 6a and 6b according to another embodiment of the present disclosure.
Figure 8B:
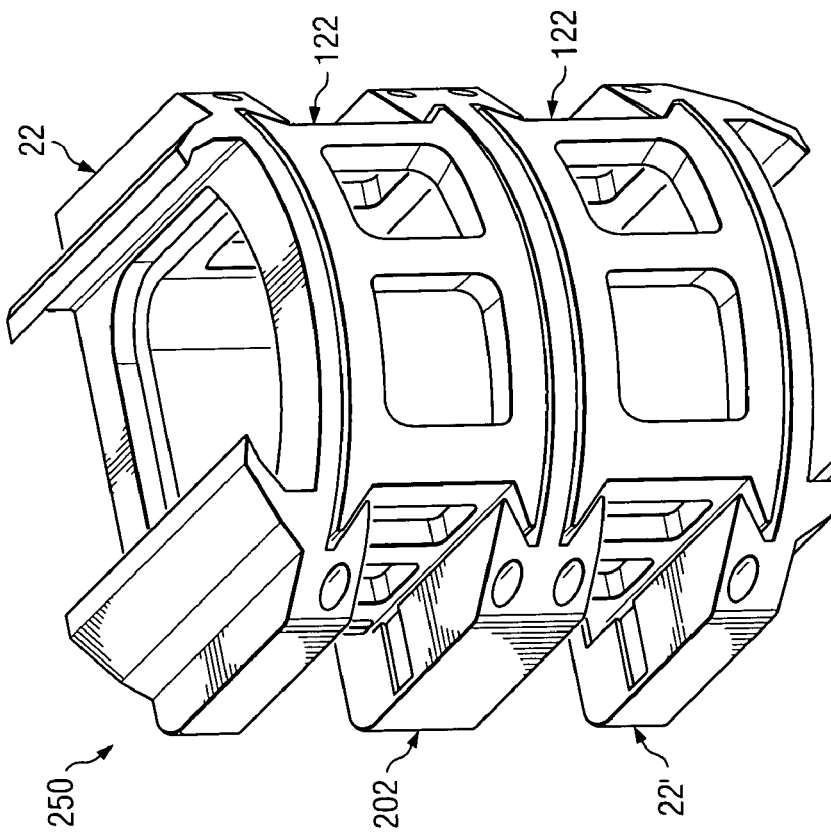

As can be appreciated, the modular stackable prosthetic joint 204 can be modified into a variety of other modular stackable prosthetic devices. For example, referring now to FIGS. 8a and 8b, the motion-preserving devices 30 of FIGS. 7a and 7b can be replaced with a pair of fusion cages substantially similar to the fusion cage 122 of FIGS. 4a and 4b. Thus, the modular stackable prosthetic joint 204 of FIGS. 7a and 7b can be revised into a modular stackable prosthetic fusion device 250.

Figure 9B:
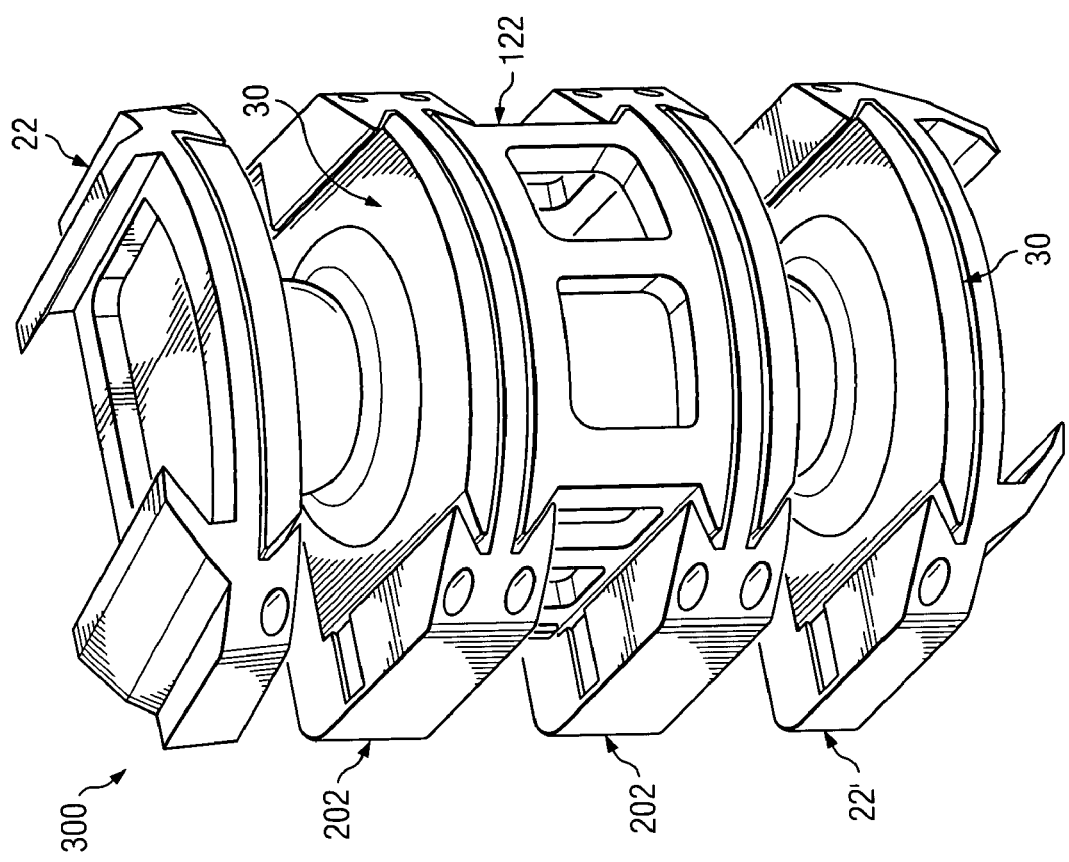
Figure 9A:
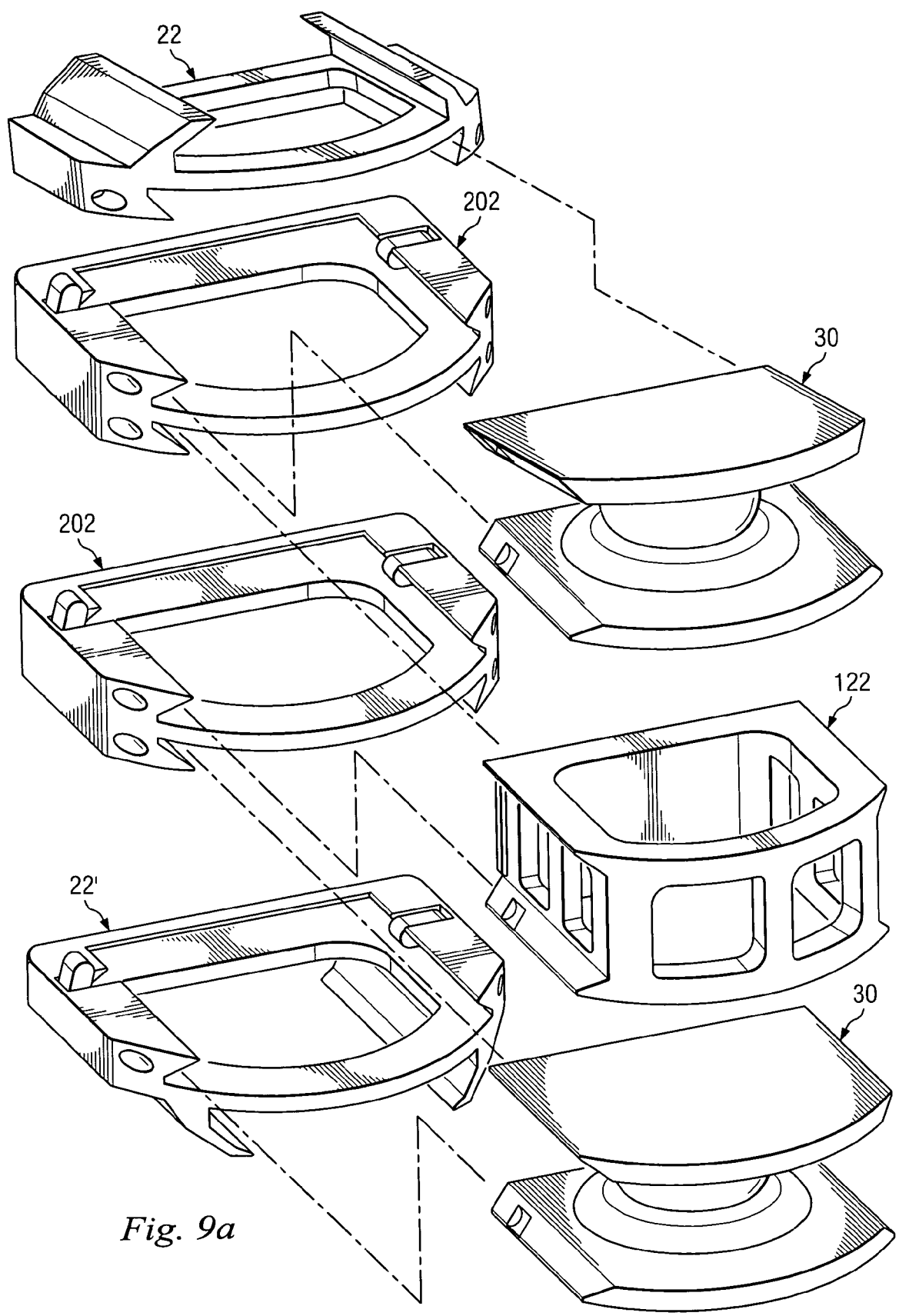
FIG. 9a is an exploded view of a modular prosthetic device incorporating the end members of FIGS. 2a and 2b and a pair of the stacking members of FIGS. 6a and 6b according to another embodiment of the present disclosure.

The modular stackable prosthetic joint 204 and/or the modular stackable prosthetic fusion device 250 may be revised to include an additional stacking member 202. Referring now to FIGS. 9a and 9b, a modular stackable prosthetic device is generally referred to by the reference numeral 300 and includes a pair of motion-preserving devices substantially similar to the motion-preserving device 30, a fusion cage substantially similar to the fusion cage 122, a pair of stacking members 202 disposed between the fusion cage 122 and the motion-preserving devices 30 and a pair of end members 22, 22'. Thus, as is evident, any combination of motion-preserving devices or fusion devices, or any other type insertion devices, is contemplated as being disposed between the end members 22, 22' along with any number of stacking members 202 to provide a revisable stackable prosthetic device.

Figure 10A:
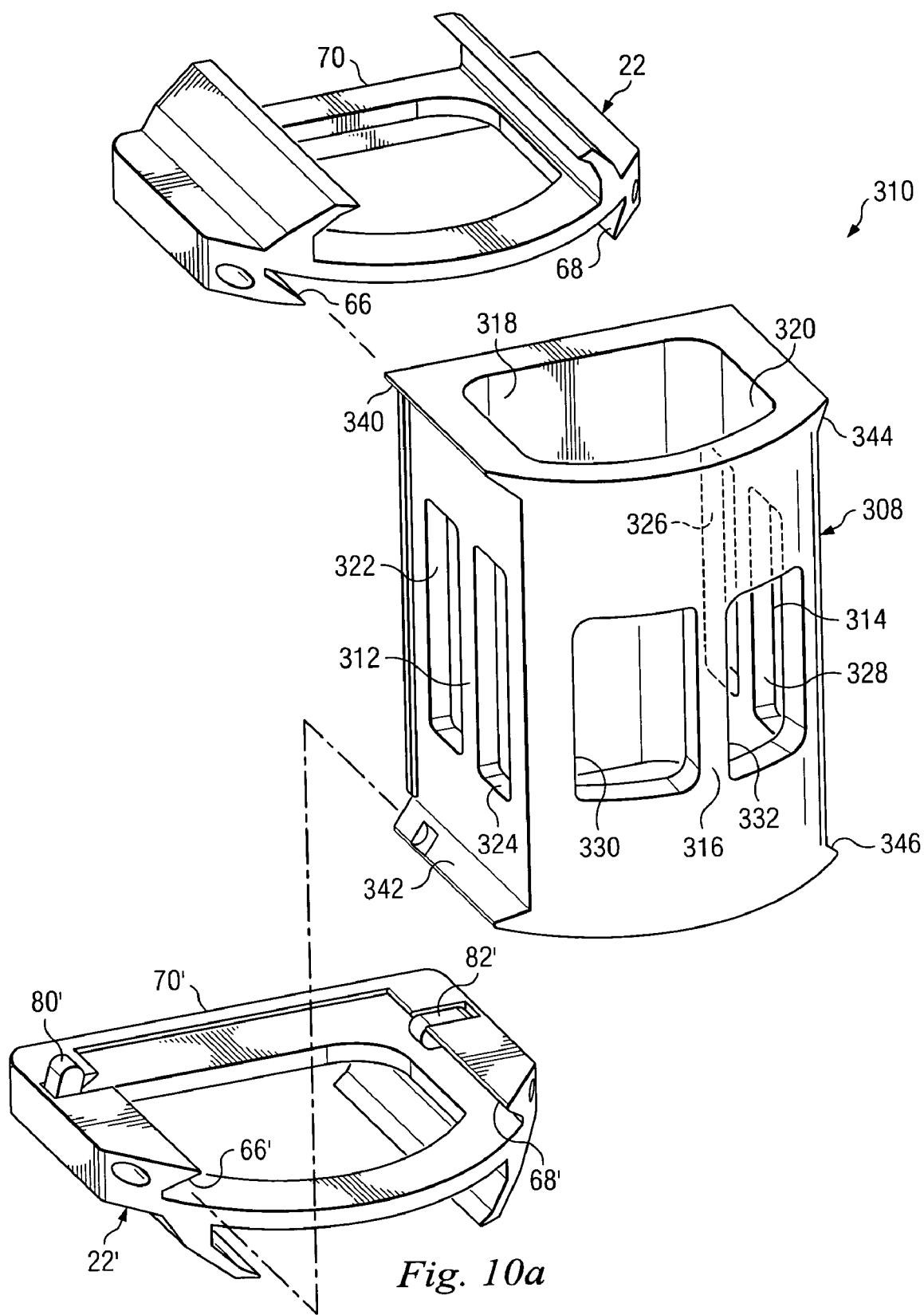
FIG. 10a is an exploded view of a modular prosthetic device incorporating the end members of FIGS. 2 and 2b according to another embodiment of the present disclosure.
Figure 10B:
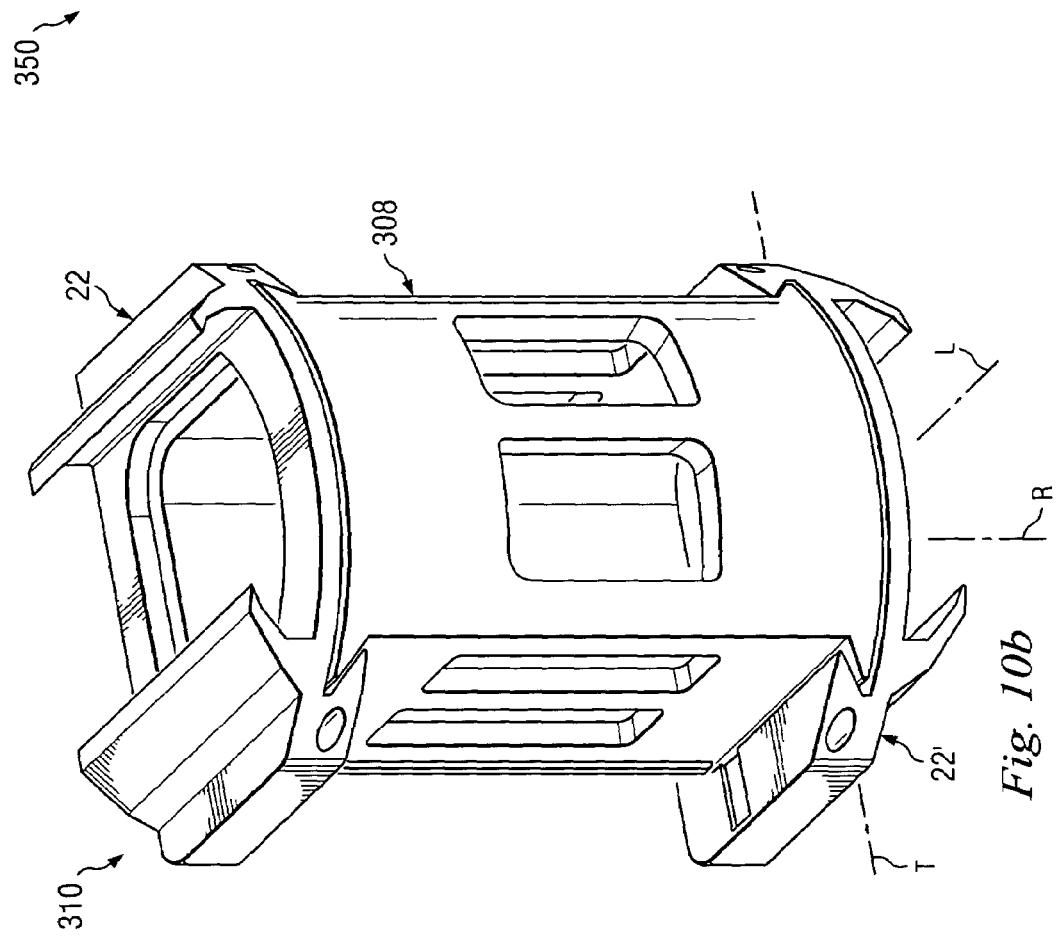

In another embodiment of the present disclosure, it is contemplated that the stacking member/members 202 may be removed, yet the anchoring device 20 is still adaptable for use in a space such as space S2 (FIG. 5). For example, and referring to FIGS. 10a and 10b, an elongated fusion cage 308 may be inserted between the end members 22, 22' to form an alternative modular prosthetic fusion device 310 such that fusion between $V_1$, $V_2$ (FIG. 5) can be effected.

The fusion cage 308 may be formed of a variety of materials including, but not limited to, PEEK, stainless steel, UHMWPE, cobalt chrome, zirc coated materials and ceramics. In one embodiment, the fusion cage 308 is a unitary structure that includes a pair of elongated lateral walls 312, 314, an elongated anterior wall 316 and an elongated posterior wall 318, all of which define an opening 320 through the fusion cage 308 along a rotational axis R. The opening 320 promotes fusing bone growth between the vertebral bodies $V_1$, $V_2$ (FIG. 5). A plurality of apertures 322, 324, 326, 328, 330, 332 may be formed through the lateral 312, 314 and anterior 316 walls to further encourage bone growth. Like the end members 22, 22', the fusion cage 308 may be coated with a bone-growth promoting substance, such as, for example, a hydroxyapatite coating formed of calcium phosphate. Additionally, the fusion cage 308 may be roughened prior to being coated with the bone-growth promoting substance to further enhance bone on-growth. Such surface roughening may be accomplished by way of, for example, acid etching, knurling, application of a bead coating, or other methods of roughening that would occur to one of ordinary skill in the art.

To accommodate insertion of the fusion cage 308 into the end members 22 and 22', a tapered extension 340, 342, 344, 346 extends longitudinally along a substantial portion of each edge of each lateral wall 312, 314. The tapered extensions 340, 344 are adapted to fit into the slots 66, 68 of the end member 22 and the tapered extensions 342, 346 are adapted to fit into the slots 66', 68' of end member 22'. The tapered extensions 340, 342, 344, 346 and the slots 66, 66', 68, 68' may have any number of configurations so long as the slots can receive the fusion cage 308 in a corresponding engagement.

In operation, the modular prosthetic fusion device 310 may be assembled by preparing the end members 22 and 22' to receive the fusion cage 308 by actuating the cam devices 80, 80', 82, 82' to an open position. The tapered extensions 340, 342, 344, 346 of the fusion cage 308 are then aligned with the slots 66, 66', 68, 68' of the end members 22, 22' and the fusion cage 308 is inserted into the end members to the point of making contact with the posterior walls 70, 70'. The cam devices 80, 80', 82, 82' are then actuated via a tool (not shown) to a closed position, thereby securing the fusion cage 308 to the end members 22, 22'.

Figure 11B:
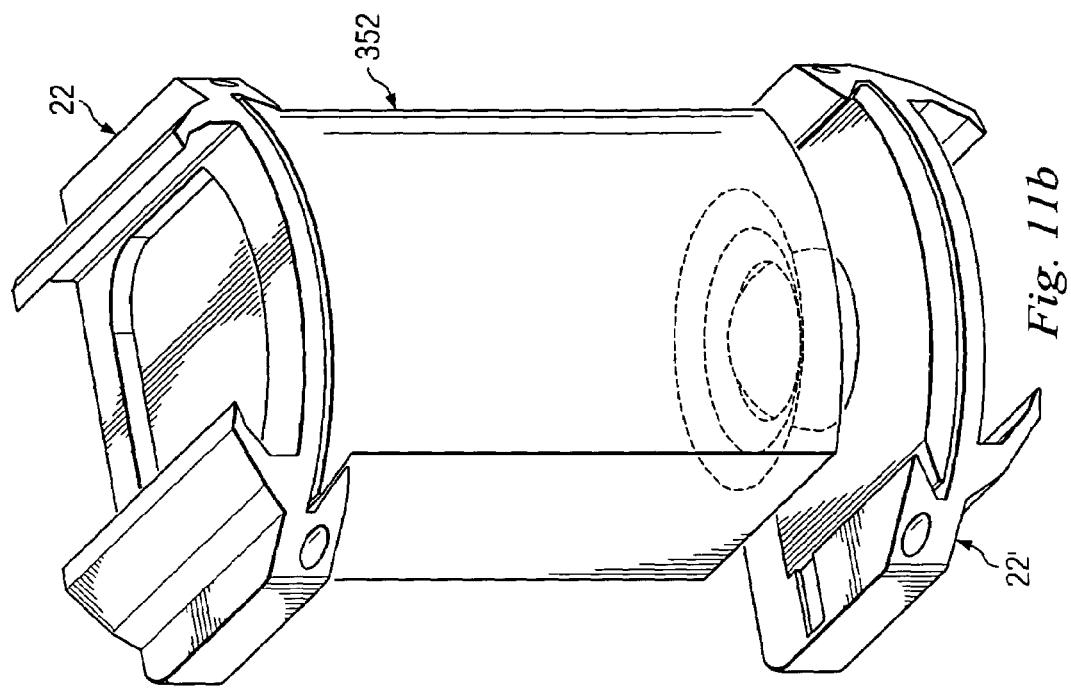
Figure 11A:
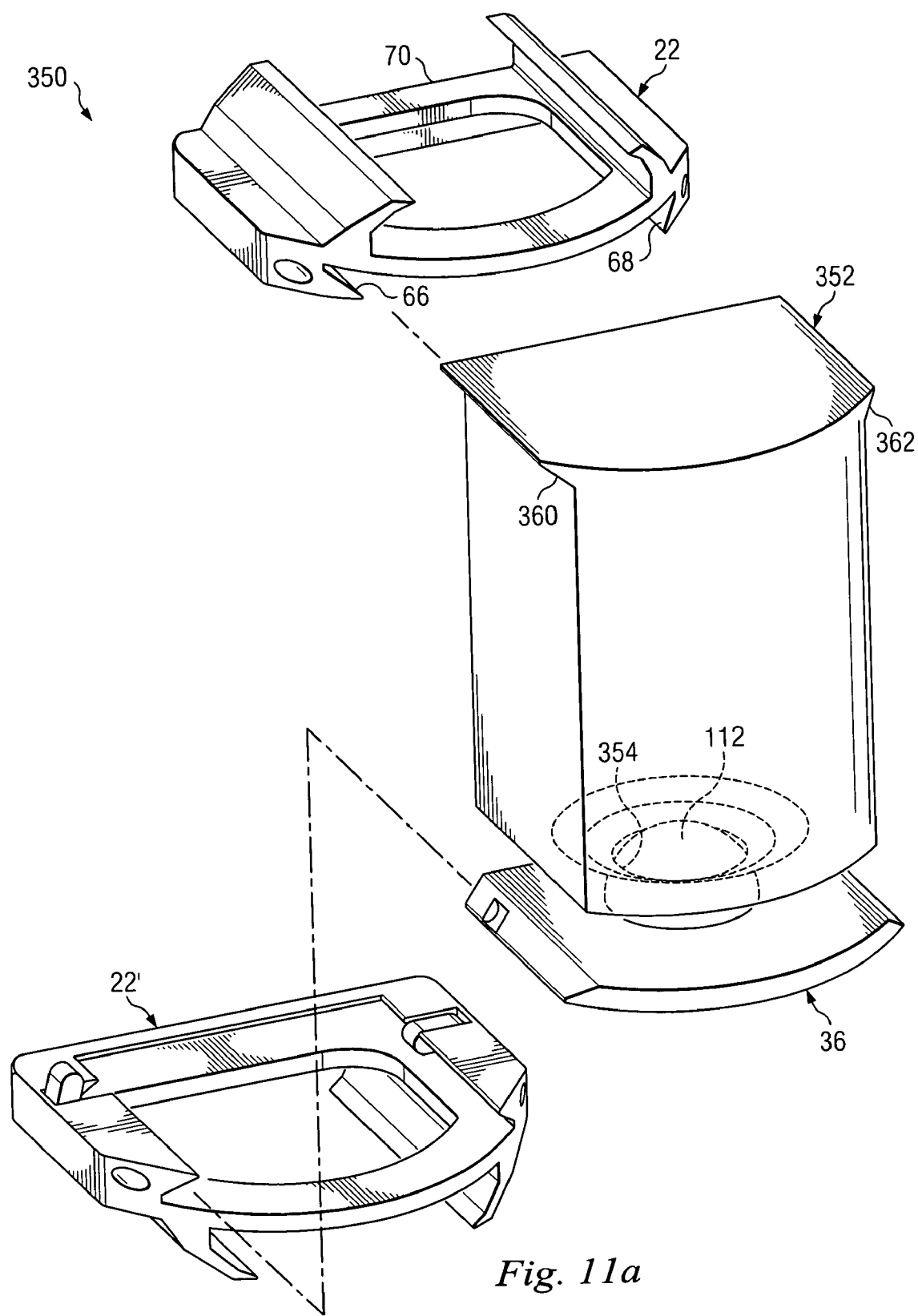
FIG. 11a is an exploded view of a modular prosthetic device incorporating the end members of FIGS. 2a and 2b according to another embodiment of the present disclosure.

In some embodiments, a modular prosthetic device incorporating the anchoring device 20 may be revised to include a corpectomy device and a motion-preserving component. Referring to FIGS. 11a and 11b, an alternative modular prosthetic device is generally referred to by reference numeral 350 and includes an elongated solid device 352 and a ball component substantially similar to the ball component 36 disposed between the end members 22, 22'. The solid device 352 includes a recess 354 formed in a lower portion (as viewed in FIGS. 11a and 11b) thereof such that the solid device may receive the corresponding projection 112 of the ball component 36.

The solid device 352 further includes a pair of tapered extensions 360, 362 for fitting to the slots 66, 68 of end member 22. Of course, the tapered extensions 360, 362 and the slots 66, 68 may have any number of configurations so long as the slots can receive the solid device 352 in a corresponding engagement.

In operation, the modular prosthetic device 350 may be assembled by preparing the end member 22 to receive the solid device 352 by actuating the cam devices (not shown) to an open position. The tapered extensions 360, 362 of the solid device 352 are then aligned with the slots 66, 68 of the end member 22 and the solid device 352 is inserted into the end member to the point of making contact with the posterior wall 70. The cam devices (not shown) are then actuated via a tool (not shown) to a closed position, thereby securing the solid device 352 to the end member 22. It is understood that the ball component 36, in the embodiment of FIGS. 11a and 11b, is secured to the end member 22' in substantially the same manner as that described with reference to FIGS. 3a and 3b. Thus, in the above-described arrangement, the modular prosthetic device 350 provides for articulating motion at only one end of the space S2 (FIG. 5), which may provide a relatively more stable arrangement.

Figure 12A:
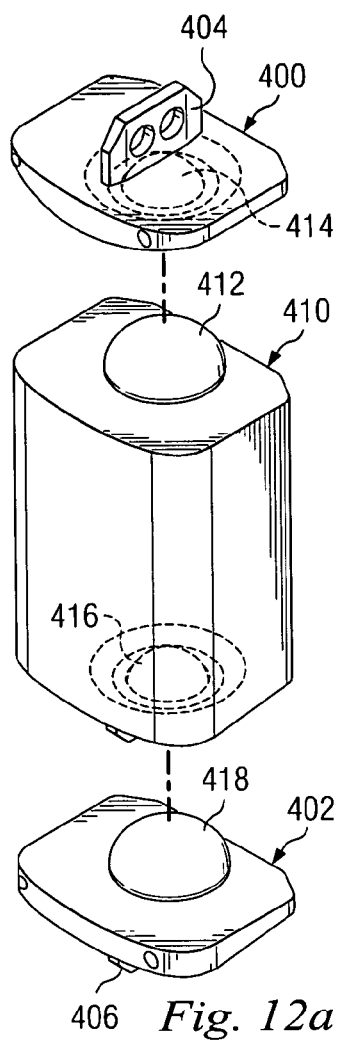
FIG. 12a is an exploded view of a modular prosthetic device according to another embodiment of the present disclosure.

Referring to FIG. 12a, in an alternative embodiment, the anchoring device 20 of the previous embodiments may be replaced with socket and ball components 400, 402 that each include a keel 404, 406, respectively, for engaging the vertebral bodies $V_1$, $V_2$ (FIG. 5), respectively. In one embodiment, except for the inclusion of the keels 404, 406, the socket and ball components 400, 402 are substantially similar to the socket and ball components 34, 36 as described with respect to FIGS. 3a and 3b. Such socket and ball components 400, 402 are described more fully in U.S. Provisional Application No. 60/446,963 filed on Feb. 12, 2003, which is herein incorporated by reference for all legitimate purposes. A spacer device 410 is provided between the socket and ball components 400, 402 and includes a projection 412 corresponding to a recess 414 formed in the socket component 400. The spacer device 410 also includes a recess 416 corresponding to projection 418 extending from the ball component 402.

Figure 12C:
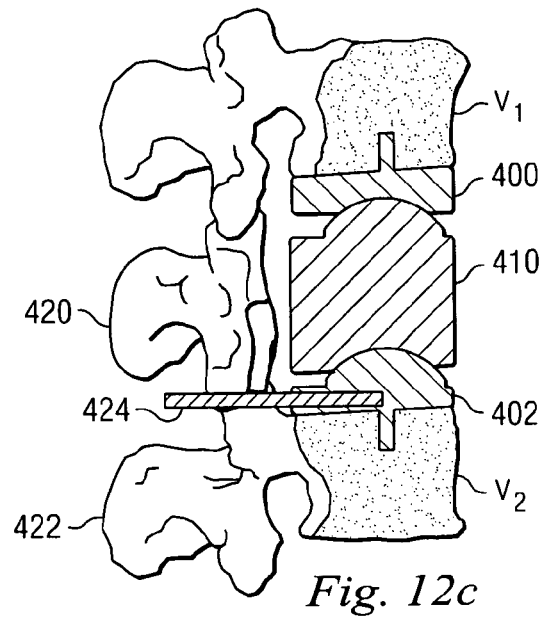
FIG. 12c is a lateral view of the prosthetic device of FIG. 12b connected to a verterbral body.
Figure 12B:
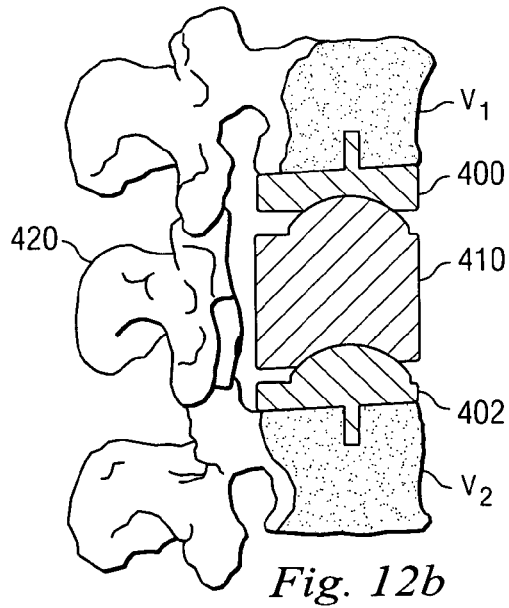
FIG. 12b is a lateral view depicting the prosthetic device of FIG. 12a disposed between a pair of vertebral bodies.

Referring to FIG. 12b, the socket and ball components 400, 402 are shown laterally engaged with the vertebral bodies $V_1$, $V_2$, respectively, and the spacer device 410 is shown engaged with the socket and ball components. It is understood that the socket and ball components 400, 402 may be inserted into the vertebral bodies $V_1$, $V_2$ from a variety of approaches other than the lateral approach, such as the anterior, transforaminal or anterior-oblique approaches. As is also illustrated, the spacer device 410 is positioned adjacent to a floating arch 420, the floating arch being the portion of vertebral body that remains after a vertebrectomy. The length of the spacer device 410 allows the spacer device to span between the socket and ball components 400, 402, thereby allowing articulating motion at both vertebral bodies $V_1$, $V_2$.

Figure 12D:
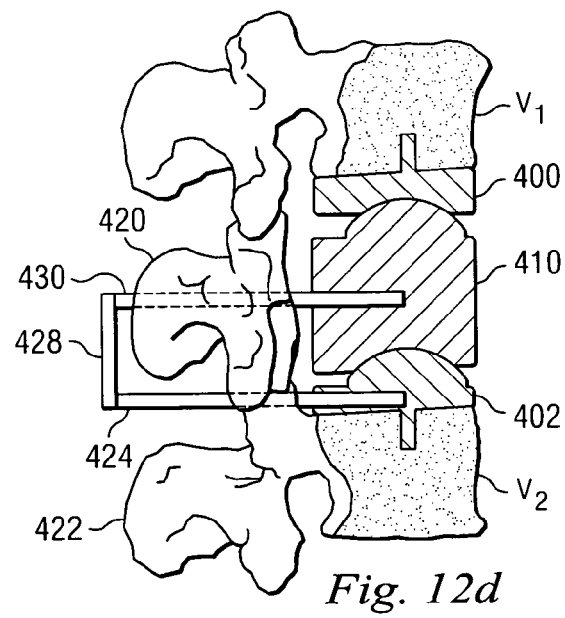
FIG. 12d is a lateral view of the prosthetic device of FIG. 12b connected to a linkage system.

In some instances, it may be desirable to revise the arrangement of FIG. 12b in order to obtain a more stable interaction between the vertebral bodies $V_1$, $V_2$ and the prosthetic devices 400, 402, 410. Referring to FIG. 12c, in one embodiment, either of the socket and ball components 400, 402 can be secured to an adjacent vertebral bone, such as an arch 422, via a linkage 424. In another embodiment, and referring to FIG. 12d, the linkage 424 may also be secured to a posterior plate 428, which, is secured to another linkage 430. The linkage 430 can be configured to engage the spacer device 410. In either arrangement, motion is provided at only one of the vertebral bodies $V_1$, $V_2$, which provides for a more stable arrangement. It is understood that the linkages 424 and 430 and the posterior plate 428 can be formed of any bio-compatible material and that the various connections between the linkages and the posterior plate and between the linkages and the prosthetic devices can be accomplished by way of threaded, slotted or any other type of conventional connection means. Furthermore, it is understood that any number of fixation systems are contemplated for use with the embodiments of FIGS. 12c and 12d, such as Antares, Z-Plate and CD Horizon fixation systems.

Although not depicted, in another embodiment, stabilization can be achieved by removing the spacer device 410 and elongating either of the socket and ball components 400, 402 such that the socket and ball components engage one another in an articulating arrangement. Thus, motion would again only be provided at one of the vertebral bodies $V_1$, $V_2$, which would result in a relatively stable arrangement.

In other instances, it may be desirable to revise the arrangement of FIG. 12b in order to obtain a more mobile interaction between the vertebral bodies $V_1$, $V_2$ and the prosthetic devices 400, 402, 410. Although not depicted, it is contemplated that the spacer device 410 may be provided with a socket and ball arrangement to provide a third articulating segment between the vertebral bodies $V_1$, $V_2$.

The present disclosure has been described relative to several preferred embodiments. Improvements or modifications that become apparent to persons of ordinary skill in the art after reading this disclosure are deemed within the spirit and scope of the application. For example, the various prosthetic insertion devices described above can be altered according to specific conditions such as lordosis and kyphosis, and thus it is contemplated that the above embodiments can be adapted for implementation into patients having varying spinal orientations. Moreover, other prosthetic insertion devices are contemplated for use with the anchoring device 20 and the stacking member 202 other than those prosthetic insertion devices illustrated and described above. Still further, the above spatial references, such as "inner," "outer," "upper," "lower," "anterior," "posterior," and "lateral" are for the purpose of illustration only and do not limit the specific orientation or location of the structure described above. Accordingly, it is understood that several modifications, changes and substitutions are intended in the foregoing disclosure and, in some instances, some features of the disclosure will be employed without a corresponding use of other features. Accordingly, it is appropriate that the appended claims be construed broadly and in a manner consistent with the scope of the disclosure.

What is claimed is:

1. An anchoring device for disposition within an intervertebral space, comprising:
   first and second end members, the first and second end members cooperating to slidably receive a prosthetic insertion device,
   wherein the first and second end members each comprise
      a first surface, at least one vertebral-engaging member extending from the first surface,
      a second surface in an opposed relation to the first surface, a first sidewall, a second sidewall, and a back wall extending from the second surface to define a socket adapted to receive a portion of the prosthetic insertion device; and
   at least one retention member having a first end and an engagement portion, the first end attached to a portion of the end member, the at least one retention member rotatable between a first position wherein the engagement portion is positioned outside of the socket for allowing the portion of the prosthetic insertion device to slide within the socket and a second position wherein the engagement portion is positioned at least partially within the socket to inhibit sliding of the portion of the prosthetic insertion device within the socket.

2. The anchoring device of claim 1 wherein the at least one retention member comprises at least one cam device.

3. The anchoring device of claim 2 further comprising an access hole for accessing the cam device for selectively rotating the retention member between first position and the second position.

4. The anchoring device of claim 1 wherein the at least one vertebral-engaging member is at an oblique angle relative to the first surface.

5. The anchoring device of claim 1 wherein the at least one vertebral-engaging member comprises a sharp edge.

6. The anchoring device of claim 1 wherein the at least one vertebral-engaging member and the first surface are coated with a bone-growth promoting substance.

7. The anchoring device of claim 6 wherein the bone-growth promoting substance is hydroxyapatite.

8. The anchoring device of claim 6 wherein the at least one vertebral-engaging member and the first surface are roughened prior to being coated with the bone-growth promoting substance.

9. The anchoring device of claim 1 wherein the second member is inverted relative to the first member.

10. The anchoring device of claim 1 wherein the first and second sidewalls extend along the second surface from a front portion to a rear portion of the second surface.

11. The anchoring device of claim 10 wherein the first and second sidewalls are substantially parallel.

12. The anchoring device of claim 11 wherein the back wall extends substantially transverse to the first and second sidewalls.

13. The anchoring device of claim 1 further comprising a hole formed through each of the first and second end members.

14. An anchoring device for receiving a prosthetic insertion device, comprising:
a first end member, comprising:
a first surface in an opposed relation to a substantially parallel second surface;
a pair of vertebral-engaging members extending from the first surface, the vertebral-engaging members being angled towards one another;
a pair of flanges extending from the second surface, the flanges being angled towards one another to define a pair of elongated slots, the pair of elongated slots adapted to slidably receive a portion of the prosthetic insertion device; and
a pair of retaining devices positioned adjacent the elongated slots, the retaining devices moveable between a first position for allowing the prosthetic insertion device to slide within the pair of elongated slots and a second position for limiting the motion of the prosthetic insertion device within the pair of elongated slots;
a second end member cooperating with the first end member to slidably receive the prosthetic insertion device, the second end member comprising:
a first surface in an opposed relation to a substantially parallel second surface;
a pair of vertebral-engaging members extending from the first surface, the vertebral-engaging members being angled towards one another;
a pair of flanges extending from the second surface, the flanges being angled towards one another to define a pair of elongated slots, the pair of elongated slots adapted to slidably receive a portion of the prosthetic insertion device; and
a pair of retaining devices positioned adjacent the elongated slots, the retaining devices moveable between a first position for allowing the prosthetic insertion device to slide within the pair of elongated slots and a second position for limiting the motion of the prosthetic insertion device within the pair of elongated slots.

15. An anchoring device for placement within an intervertebral space and for receiving a prosthetic insert, the anchoring device comprising:
first and second end members, the first and second end members cooperating to slidably receive the prosthetic insert, wherein the first and second end members each comprise
a first surface for engaging a vertebra;
at least one vertebral-engaging member extending from the first surface;
a second surface in an opposed relation to the first surface;
a pair of flanges extending from the second surface, the flanges being angled towards one another to define a pair of elongated slots, the pair of elongated slots adapted to slidably receive a portion of the prosthetic insert; and
a pair of retaining members positioned adjacent the elongated slots and moveable between a first position for allowing the prosthetic insert to slide within the pair of elongated slots and a second position for limiting the motion of the prosthetic insert, wherein the retaining members are aligned substantially transverse to a plane extending substantially along and between the pair of elongated slots when in the first position, and wherein the retaining members are aligned substantially parallel to the plane when in the second position.

16. The anchoring device of claim 15 wherein at least one of the pair of retaining devices comprises a cam device.

17. The anchoring device of claim 16 wherein the cam device is rotatable between the first position and the second position.

18. The anchoring device of claim 17 further comprising an access hole for accessing the cam device and selectively rotating the cam device between the first position and the second position.

19. The anchoring device of claim 15 wherein the at least one vertebral-engaging member is at an oblique angle relative to the first surface.

20. The anchoring device of claim 15 wherein the first surface and the at least one vertebral-engaging member are coated with a bone-growth promoting substance.

21. The anchoring device of claim 15 wherein at least one of the first and second members further comprises a wall extending substantially transverse to the pair of flanges to limit the travel of the prosthetic insert.

22. The anchoring device of claim 15 wherein the pair of retaining members are attached to the end member.

23. The anchoring device of claim 22 wherein the pair of retaining members are pivotally attached to the end member.

24. A system for securing a prosthetic insert within an intervertebral space, comprising:
a first end member comprising:
a first surface,
at least one vertebral-engaging member extending from the first surface,
a second surface in an opposed relation to the first surface,
a first sidewall, a second sidewall, and a back wall extending from the second surface to define a first socket adapted to receive a first portion of the prosthetic insertion device,
at least one retention member having a first end and an engagement portion, the first end attached to a portion of the end member, the at least one retention member selectively rotatable between a first position wherein the engagement portion is positioned outside of the first socket for allowing the first portion of the prosthetic insert to slide within the first socket and a second position wherein the engagement portion is positioned at least partially within the first socket to inhibit sliding of the first portion of the prosthetic insert within the first socket, and
a tool receiving aperture for accessing the at least one retention member; and
a tool having a working end sized to fit at least partially within the tool receiving aperture of the end member, wherein the tool is adapted to selectively rotate the at least one retention member between the first position and the second position.

25. The system of claim 24, further comprising
a second end member comprising:
a first surface,
at least one vertebral-engaging member extending from the first surface,
a second surface in an opposed relation to the first surface, a first sidewall, a second sidewall, and a back wall extending from the second surface to define a second socket adapted to receive a second portion of the prosthetic insertion device.

26. The system of claim 25 wherein the second end member further comprises at least one retention member having a first end and an engagement portion, the first end attached to a portion of the end member, the at least one retention member selectively rotatable between a first position wherein the engagement portion is positioned outside of the second socket for allowing the second portion of the prosthetic insert to slide within the second socket and a second position wherein the engagement portion is positioned at least partially within the second socket to inhibit sliding of the second portion of the prosthetic insert within the second socket.

27. The system of claim 26 wherein the second end member further comprises a tool receiving aperture for receiving the tool for selectively rotating the at least one retention member between the first position and the second position.

* * * * *